United States Patent
Koelm et al.

(10) Patent No.: US 9,958,426 B2
(45) Date of Patent: May 1, 2018

(54) DEVICE AND METHOD FOR DETERMINING MIXING RATIOS OF FLOWING MEDIA

(71) Applicant: W.O.M. World of Medicine GmbH, Berlin (DE)

(72) Inventors: Matthias Koelm, Berlin (DE); Peter Juelg, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 77 days.

(21) Appl. No.: 14/916,257

(22) PCT Filed: Aug. 25, 2014

(86) PCT No.: PCT/DE2014/000425
§ 371 (c)(1),
(2) Date: Jun. 20, 2016

(87) PCT Pub. No.: WO2015/032377
PCT Pub. Date: Mar. 12, 2015

(65) Prior Publication Data
US 2016/0305921 A1    Oct. 20, 2016

(30) Foreign Application Priority Data
Sep. 3, 2013    (DE) .................. 10 2013 014 532

(51) Int. Cl.
*G01N 33/00*    (2006.01)
*G01F 1/36*    (2006.01)
*G01F 1/68*    (2006.01)
*G01N 11/08*    (2006.01)
*G01N 7/00*    (2006.01)

(52) U.S. Cl.
CPC ............ *G01N 33/004* (2013.01); *G01F 1/36* (2013.01); *G01F 1/68* (2013.01); *G01N 7/00* (2013.01); *G01N 11/08* (2013.01)

(58) Field of Classification Search
CPC .. G01F 1/36; G01F 1/68; G01N 11/08; G01N 33/004; G01N 7/00
See application file for complete search history.

(56) References Cited

U.S. PATENT DOCUMENTS

| | | | |
|---|---|---|---|
| 2,439,723 A | 4/1948 | Engdahl | |
| 4,576,043 A * | 3/1986 | Nguyen | G01F 1/74 702/47 |
| 4,905,505 A * | 3/1990 | Reed | G01N 7/00 73/64.46 |

(Continued)

FOREIGN PATENT DOCUMENTS

| | | |
|---|---|---|
| EP | 0022493 A2 | 1/1981 |
| EP | 1686355 A1 | 8/2006 |
| WO | 00/14484 A2 | 3/2000 |

*Primary Examiner* — Francis Gray
(74) *Attorney, Agent, or Firm* — Mayer & William, PC; Stuart H. Mayer

(57) ABSTRACT

The present invention relates to a device and a method for determining mixing ratios of flowing media, in particular for determining the mixing ratios of two gases by using two flow resistances with different characteristic curves, each flow resistance containing a differential pressure sensor and being connected in series, where one flow resistance is formed by a sintered metal filter and another flow resistance is formed by an orifice.

11 Claims, 7 Drawing Sheets

(56) References Cited

U.S. PATENT DOCUMENTS

| | | | | |
|---|---|---|---|---|
| 5,161,406 A | * | 11/1992 | Heinonen | A61M 16/104 |
| | | | | 73/23.2 |
| 6,422,092 B1 | * | 7/2002 | Morrison | G01F 1/50 |
| | | | | 73/861.04 |
| 2004/0134262 A1 | * | 7/2004 | Bures | G01N 11/08 |
| | | | | 73/54.05 |
| 2009/0293634 A1 | | 12/2009 | Ong | |

* cited by examiner

Fig. 1- Illustration of measurement set-up:

Pneumatic circuit diagram measurement set-up

Fig. 2: Illustration of calibration set-up

Fig. 3: Illustration of calibration curves

Characteristic curves air and CO2 dp1_air (dp2): dp1 value that can be associated with a measurement value dp2 using the characteristic curve of air dp1_CO2 (dp2): dp1 value that can be associated with a measurement value dp2 using the characteristic curve of CO2

Simplification for determination of the dp1/(dp2) values of air and CO2

Reasons for simplification given by First Intercept Theorem

Orifice (dimensions)

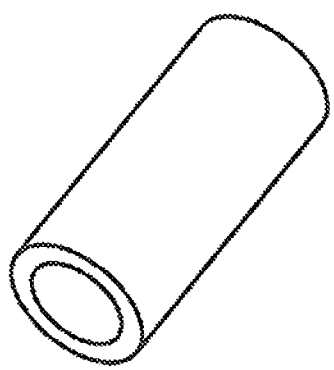
Sinter metal filter as a hollow cylinder
(viewed from outside)
Figure 7A
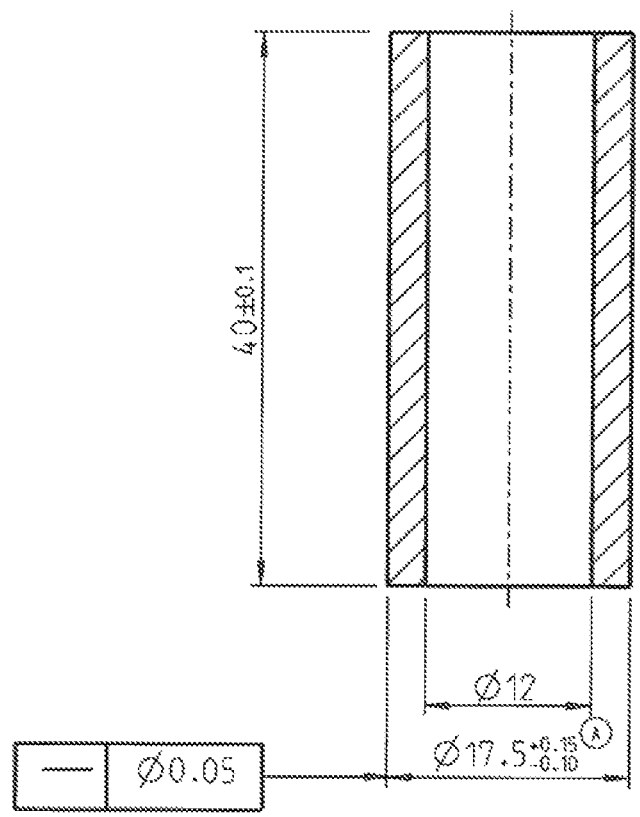
Fgure 7B
Sinter metal filter (dimensions), pore size 35µm

DEVICE AND METHOD FOR DETERMINING MIXING RATIOS OF FLOWING MEDIA

BACKGROUND OF THE INVENTION

The present invention relates to a device and a method for determining mixing ratios of flowing media, in particular for determining the mixing ratios of two gases by using two flow resistances with different characteristic curves.

The determination of the percentages of different components of fluids, for instance gas or liquid mixtures is necessary in many fields of engineering. For this purpose there exist a large variety of different methods using optical, acoustic, or electrochemical methods. Nonetheless, there is lacking a simple method for determining the mixing ratios of two fluids, in particular of two gases. Subject matter of the present invention is therefore a simple method for determining the relative portions of two components of a fluid mixture, in particular of a gas mixture, and a device suitable therefor.

Thus, the present invention teaches a device according to claim 1 and a method according to claim 6 carried out by means of said device. Advantageous embodiments of the invention are subject matter of subclaims referred thereto.

SUMMARY OF THE INVENTION

The exemplary device described in the following and the method carried out by means of said device is capable to precisely indicate the relative constituents of a gas mixture, e.g., the percentages of $CO_2$ and nitrogen in a gas mixture. The invention is based on the fact that there exist flow resistances with different characteristic curves. Examples are a sintered metal filter and an orifice. The flow resistance of a sintered metal filter has a nearly linear characteristic curve, i.e., the flow resistance increases nearly linearly with the velocity of flow. In contrast, an orifice has a nearly square characteristic curve, i.e., the flow resistance increases nearly with the square of the velocity of flow.

These different characteristic curves can presumably be ascribed to different flow conditions when passing the filter: It can be assumed that within the sintered metal filter the flow is nearly laminar, so that the flow resistance is substantially determined by the viscosity of the gas. In contrast, the flow at an orifice will be turbulent, so that the flow resistance is mainly determined by the density of the gas. However, these are merely theoretical considerations, without claiming absolute truth. In any case, the above exemplary orifice may be replaced by other flow resistances, too, for instance by restrictions, valves, bends, wedge elements, or venturis. The sintered metal filter, too, may be replaced by other devices, which ensure a nearly laminar flow.

As an alternative for the measurement of the differential pressure, measurement of the mass flow, for instance by means of a thermal gas flow sensor, may also be utilized.

It was found that the present method, by means of the device according to the invention, allows the measurement of the constellation portions of two gases, e.g., of a mixture of nitrogen and helium, oxygen and $CO_2$, CO and $H_2$, or $NH_3$ and $H_2$. Furthermore, it is also possible to analyze more complex gas mixtures, for instance mixtures of "air" and $CO_2$. The condition is, however, that the mixing ratios of air (or another gas mixture) are constant. In the example of the mixing ratio of "air" and $CO_2$, further, the "natural" $CO_2$ portion of the air (approx. 0.04%) is neglected.

BRIEF DESCRIPTION OF THE DRAWINGS

FIGS. 7A and 7B show a sintered metal filter hollow cylinder made from Cr—Ni-steel. FIG. 7A shows a sinter metal filter as a hollow cylinder (view from the outside) and FIG. 7B shows a sinter metal filter with a pore size of 35 μm.

DETAILED DESCRIPTION OF THE INVENTION

Theoretical Approach

Due to the dependence of the flow resistances on the flow properties of the medium, the composition of gas mixtures can be determined. The condition is that the flow properties of the gases do not significantly differ. In principle, this correlation also applies for liquids.

Measurement and Calibration Set-Up

For determining the concentration ratios, the medium is conducted through a series connection of two flow resistances. The respective differential pressure drop over the flow resistance is recorded and used as a basis for determining the concentration ratios. The condition for the differentiation of different media portions is the use of two flow resistances with different characteristic curves, e.g., linear and square. In the measurement set-up shown here, this is achieved by a sintered metal filter (linear) and an orifice (square). Furthermore, by means of a pressure sensor, the absolute pressure (p_abs) is obtained, by means of which errors caused by pressure variations are compensated (see below). Another aspect of the set-up is a temperature measurement of the gas for correcting any potential temperature variations (see below).

Figure 1:
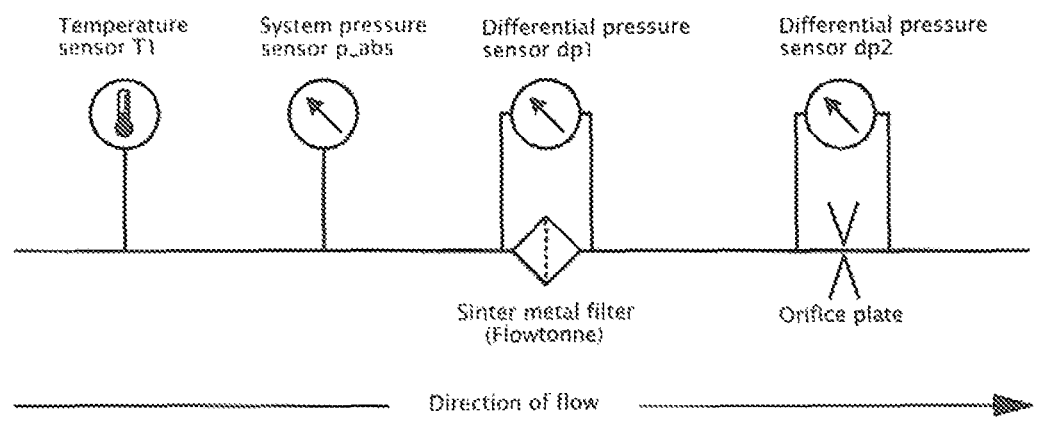
FIG. 1 shows an illustration of pneumatic circuit measurement set-up.
Figure 2:
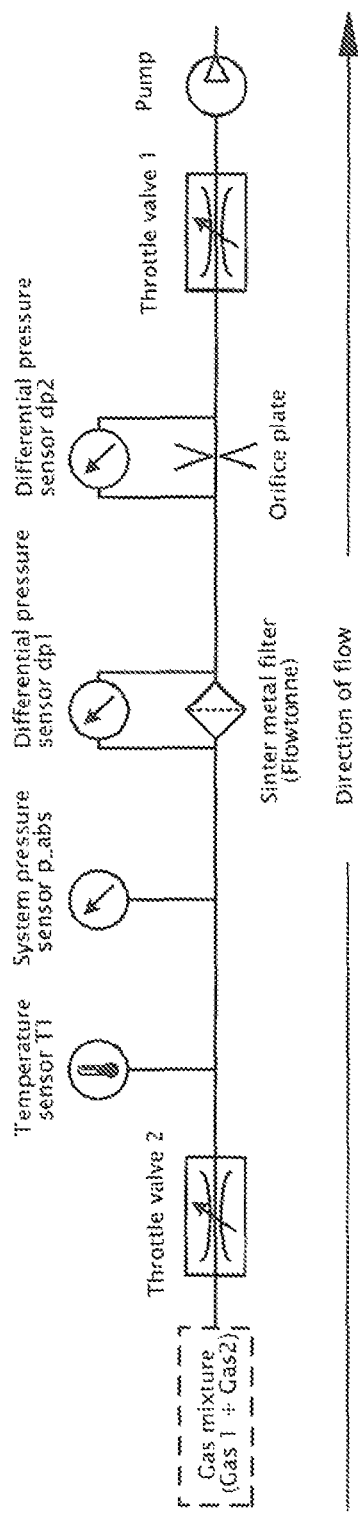
FIG. 2 shows an illustration of calibration set-up.

For using the measurement set-up, a prior calibration with the corresponding media is required. This is necessary for both mixture components to be measured. An exemplary set-up for calibration is shown in FIG. 2. By plotting the differential pressure dp1 versus the differential pressure dp2, a characteristic curve is generated for the medium (FIG. 3), which is used for the later calculation of the concentration percentages (see below).

For generating a volume flow, a pneumatic pump is employed, with the control of the volume flow being effected by a throttle valve 1. The throttle valve 2 serves for generating different underpressure levels over the complete measurement path, for determining the parameters of the absolute pressure correction (see below).

Figure 3:
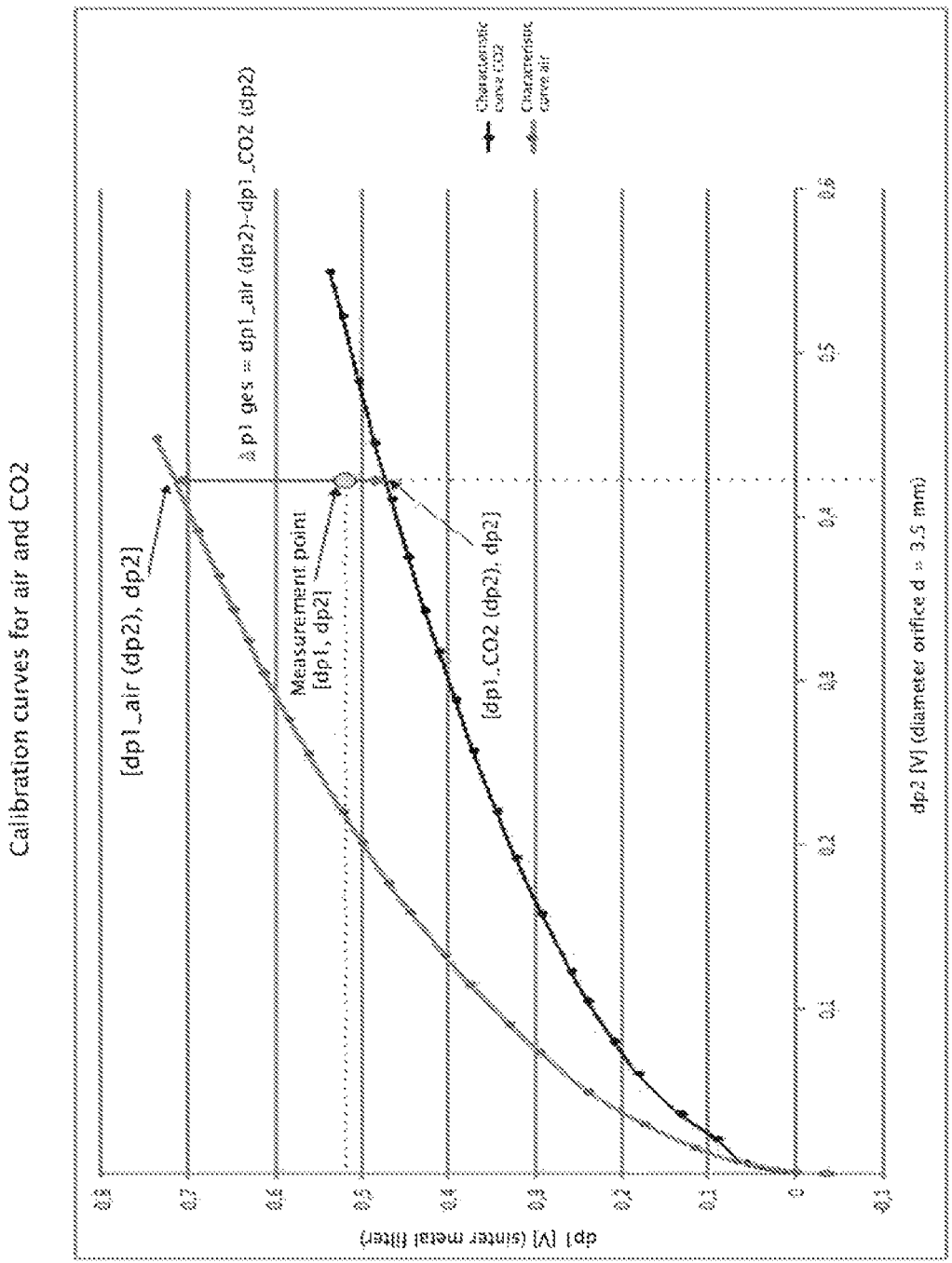
FIG. 3 shows calibration curves for air and $CO_2$.

In the example of the gas mixture of gas 1 and gas 2 to be measured here, a calibration is made with pure gas 1 or pure gas 2. The characteristic curves determined from such a mixture are shown in FIG. 3 as an example of a mixture of air (gas 1) and $CO_2$ (gas 2).

Herein, as an example, a calibration and subsequent measurement of an air/$CO_2$ mixture was made. The gas conduits had a diameter of 8 to 10 mm. Gas flows up to 30 l/min were achieved. Before the measurement path (see FIG.

Figure 6:
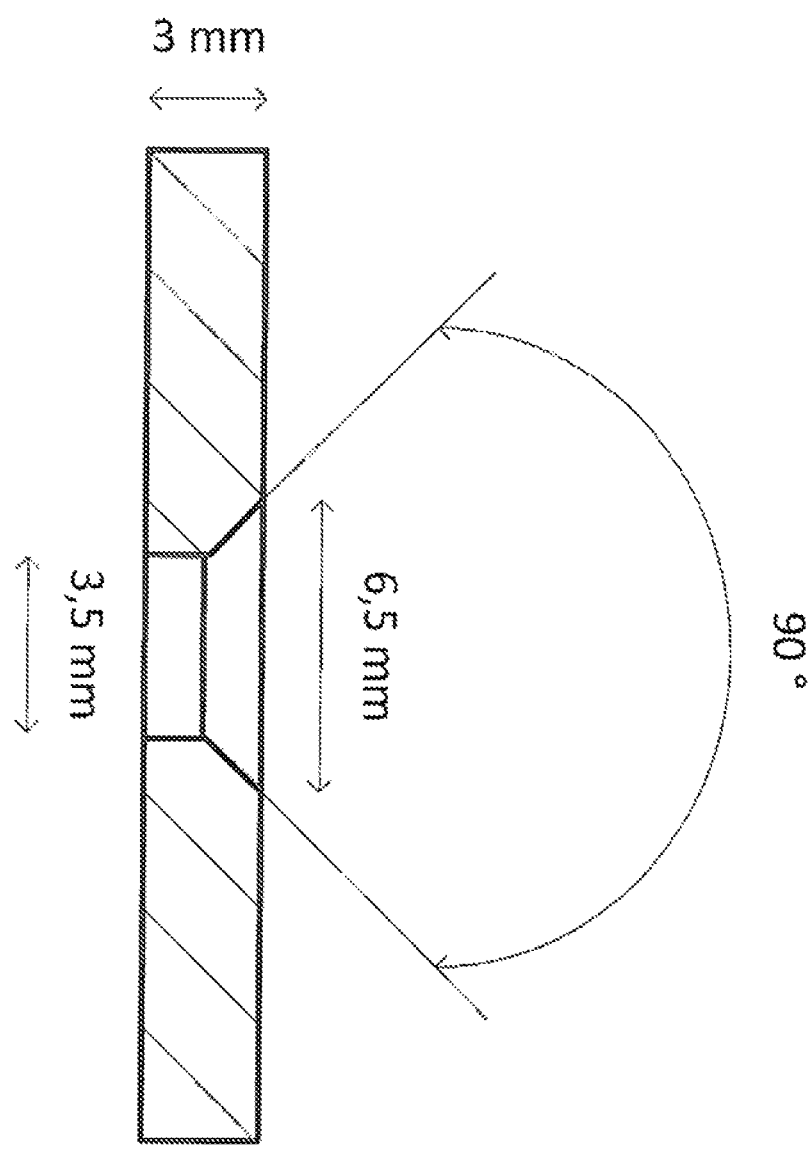
FIG. 6 shows the dimensions of an orifice.

1), pressures up to −150 mbar relative to the atmosphere were measured, by means of a sensor from the HDI series of the company Sensotronics, which operates in the range from −1 bar (−14.5 psi) to +1 bar (+14.5 psi). The differential pressure sensors over the flow resistances had a measurement range from 0 to 10 mbar (0.145 psi). For this purpose, sensors of the HDI series of the company Sensotronics were employed (HDIM010DUF8P5). As flow resistances, an orifice (FIG. 6) and a sintered metal filter (FIG. 7) with a pore size of 35 μm were used. As shown in FIG. 7, the sintered metal filter was configured in the form of a hollow cylinder made from Cr—Ni-steel.

It was found that an accuracy of the calibration being sufficient for many purposes can already be achieved by calibration with one gas only, with the characteristic curve of the second gas being calculated. This enables, for instance, a regular calibration for an air/$CO_2$ measurement by determination of the characteristic curve for air with calculation of the characteristic curve for $CO_2$. In this way, the determination of the characteristic curve of $CO_2$ being otherwise necessary can be dropped.

Basic Equations

The following equations or conditions apply:

$$R = \frac{dP}{Q} \text{ applies for small pressure variations or for linear flow resistances } R \quad \text{i.)}$$

$$\frac{c[\text{Gas 1}]}{c[CO_2]} = \frac{R_{Gas\,1}}{R_{Gas\,2}}; \quad \text{ii.)}$$

$c$ = concentration,
$R$ = flow resistance $$\frac{dp2_{Gas\,2}}{R2_{Gas\,2}} = \frac{dp1_{Gas\,2}}{R1_{Gas\,2}} \neq \frac{dp2_{Gas\,1}}{R2_{Gas\,1}} = \frac{dp1_{Gas\,1}}{R1_{Gas\,1}} \quad \text{iii.)}$$

In words: The characteristic curves of the flow resistances significantly differ depending on the media concentration.

Calculation of the Mixing Ratio for an Example Gas 1 and Gas 2

In the following calculations, the gas 2 portion is the target value to be determined. If there is a mixture of gas 1 and gas 2, the flow resistances are made up approximatively as an addition of the flow resistances $R_{Gas2}$ and $R_{Gas1}$ together:

$$R1_{misch} = n \cdot R1_{Gas1} + (1-n) \cdot R1_{Gas2}; \quad R2_{misch} = n \cdot R2_{Gas1} + (1-n) \cdot R2_{Gas2}$$

$n$ = portion of Gas1 or Gas2, $0 \leq n \leq 1$

For the measurement of a gas mixture follows from (i.):

$$\frac{dp2}{R2_{misch}} = \frac{dp1}{R1_{misch}}$$

$$\frac{dp2}{dp1} = \frac{R2_{misch}}{R1_{misch}}$$

$$\frac{dp2}{dp1} = \frac{n * R2_{Gas\,1} + (1-n) * R2_{Gas\,2}}{n * R1_{Gas\,1} + (1-n) * R1_{Gas\,2}}$$

$$\frac{dp2}{dp1} = \frac{n * R2_{Gas\,1} + R2_{Gas\,2} - n * R2_{Gas\,2}}{n * R1_{Gas\,1} + R1_{Gas\,2} - n * R1_{Gas\,2}}$$

With $$R = \frac{dp}{Q}$$

follows $$\frac{dp2}{dp1} = \frac{(n * dp2_{Gas\,1} + dp2_{Gas\,2} - n * dp2_{Gas\,2}) * Q}{(n * dp1_{Gas\,1} + dp1_{Gas\,2} - n * dp1_{Gas\,2}) * Q}$$

$$\frac{dp2}{dp1} = \frac{n * dp2_{Gas\,1} + dp2_{Gas\,2} - n * dp2_{Gas\,2}}{n * dp1_{Gas\,1} + dp1_{Gas\,2} - n * dp1_{Gas\,2}}$$

Assume a Vertical Concentration Behavior:

For the calculation of the gas concentration, the following assumption is made:

$$dp2 = dP2_{Gas2} = dP2_{Gas1}$$

Figure 4:
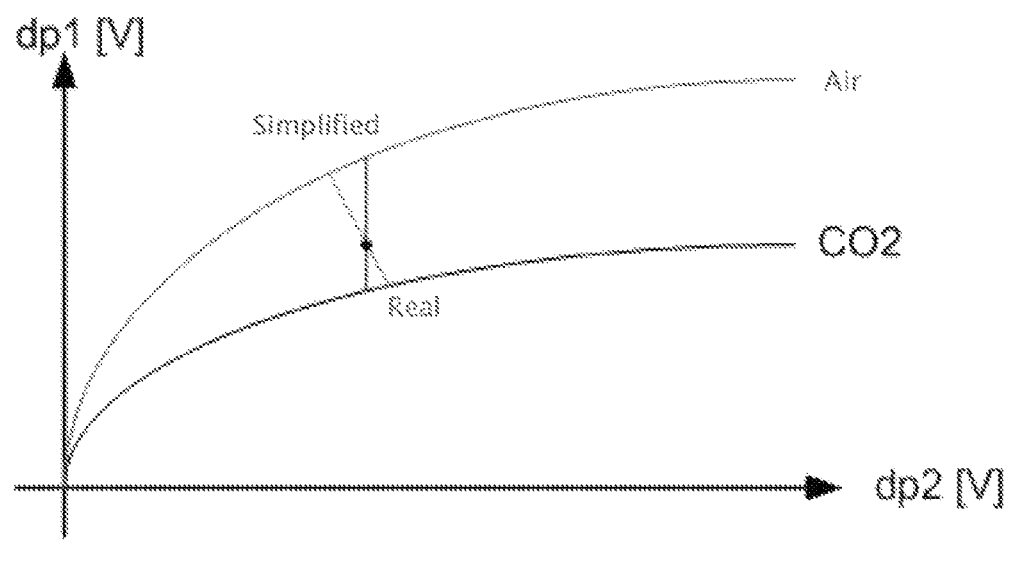
FIG. 4 shows a simplification for determining the dp1/(dp2) values of air and $CO_2$.

This corresponds to a simplification, since the real concentration behavior from one to another characteristic curve, that is, e.g., from 100% gas 2 to 100% gas 1 does not proceed vertically, but along an inclined line. This experimentally found effect is shown in FIG. 4:

This simplification for determining the gas 2 concentration is admissible, since the characteristic curves of gas 1 and gas 2 can be assumed as extending in parallel to each other in a sufficiently small interval. Thereby, then the First Intercept Theorem of elementary geometry can be applied:

If you have two lines intersecting at a common point, and the two lines are intersected by two parallels, which do not pass through the intersection point of the lines, then applies:

The ratio of the two segments of a line formed by the intersection point of the lines and the parallels equals the ratio of the corresponding segments on the second line.

Figure 5:
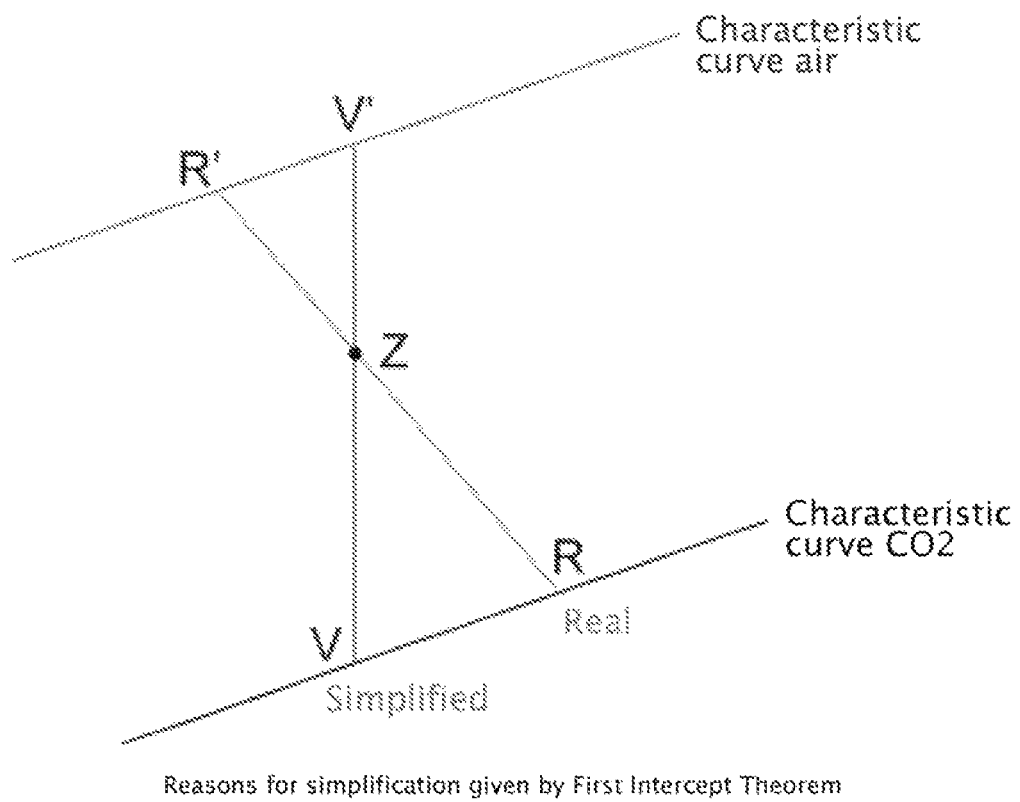
FIG. 5 shows reasons for simplification by First Intercept Theorem of elementary geometry.

Applied to the case of interest here, the following relationship shown in FIG. 5 will result (shown here, too, in an exemplary manner with reference to the characteristic curves of air and $CO_2$):

$$VZ:VV'=RZ:RR'$$

Thus follows:

$$\frac{dp2}{dp1} = \frac{n * dp2 + dp2 - n * dp2}{n * dp1_{Gas\,1} + dp1_{Gas\,2} - n * dp1_{Gas\,2}}$$

$$\frac{dp2}{dp1} = \frac{dp2}{n * dp1_{Gas\,1} + dp1_{Gas\,2} - n * dp1_{Gas\,2}}$$

$$\frac{dp2}{dp1} = \frac{dp2}{n * (dp1_{Gas\,1} - dp1_{Gas\,2}) + dp1_{Gas\,2}}$$

$$dp1 = n * (dp1_{Gas\,1} - dp1_{Gas\,2}) + dp1_{Gas\,2}$$

$$n = \frac{dp1 - dp1_{Gas\,2}}{(dp1_{Gas\,1} - dp1_{Gas\,2})}$$

$$n = \frac{dp1 - dp1_{Gas\,2}}{\Delta P1_{ges}}$$

Limiting Behavior of the Equations:

$$dp1 = dp1_{Gas2} \Rightarrow n=0 \Rightarrow \text{Gas2-content } 100\%$$

$$dp1 = dp1_{Gas1} \Rightarrow n=1 \Rightarrow \text{Gas2-content } 0\%$$

Normalization:

In order to directly indicate the gas 2 concentration, the following conversion is made:

$$Gas2\ concentration = (1-n) \cdot 100\%[Gas2]$$

$$= 1 - \frac{dp1 - dp1_{Gas\,2}}{(dp1_{Gas\,1} - dp1_{Gas\,2})} * 100\%[Gas2]$$

$$= \frac{\Delta p1_{ges}}{\Delta p1_{ges}} - \frac{dp1 - dp1_{Gas\,2}}{\Delta p1_{ges}} * 100\%[Gas2]$$

$$= \frac{(dp1_{Gas\,1} - dp1_{Gas\,2})}{\Delta p1_{ges}} - \frac{(dp1 - dp1_{Gas\,1})}{\Delta p1_{ges}} * 100\%[Gas\,2]$$

$$= \frac{(dp1_{Gas\,1} - dp1_{Gas\,2})}{\Delta p1_{ges}} + \frac{-dp1 + dp1_{Gas\,2_2}}{\Delta p1_{ges}} * 100\%[Gas\,2]$$

$$= \frac{(dp1_{Gas\,1} - dp1)}{\Delta p1_{ges}} * 100\%[Gas\,2]$$

$dp1_{Gas1}$ and $dp1_{Gas2}$ have to be determined with the respective measurement value dp2 from the calibration characteristic curves! dp1 is a measurement value.

Absolute Pressure Correction

Absolute pressure variations will lead to a change of state of the gas mixture. This is accompanied by a change of the flow properties, whereby a measurement error is caused. This error has to be corrected correspondingly. For this purpose, a correction formula is experimentally determined using the shown calibration set-up.

Temperature Correction

In an analogous manner to absolute pressure variations, a temperature variation will affect the measurement result. The correction is made by using the temperature in an experimentally determined correction formula.

Method

The method of measuring according to the invention is based therefore on the measurement of the pressure drop of a fluid flow over two flow resistances compared with a calibration curve. For carrying-out the method, the set-up device has therefore first to be calibrated by means of two fluids, for instance of two liquids or of two gases. The mentioned fluids can in turn represent mixtures, provided that the mixing ratio remains constant, such as for instance when using air. Preferred fluids are gases.

The method can be applied in different fields of engineering. For example, the composition of process gases in the chemical industry can be determined according to the invention. Those skilled in the art will of course understand that with very high flows, as it is the case in many fields of chemical engineering, an arbitrary partial flow can be separated, within which the measurement is made. A preferred application of the method according to the invention is the determination of the $CO_2$ percentage of air in medical devices, e.g., respirators or insufflators.

The invention claimed is:

1. A device for determining the fluid concentration of a flowing fluid mixture, the fluid mixture substantially containing two fluid components, wherein
    a flow conduit which contains at least two flow resistances each containing a differential pressure sensor and being connected in series, the at least two flow resistances having different characteristic curves.

2. The device according to claim 1, wherein one of the flow resistances has a linear characteristic curve and another flow resistance has a square characteristic curve.

3. The device according to claim 1, wherein one flow resistance is formed by a sintered metal filter and another flow resistance is formed by an orifice.

4. The device according to claim 1, wherein the fluid mixture is gaseous.

5. The device according to claim 4, wherein the fluid mixture contains CO2 and air.

6. A method for determining the fluid concentration of a flowing fluid mixture, the fluid mixture substantially containing two fluid components, comprising the steps of:
    a) conducting the fluid mixture through a flow conduit which contains at least two flow resistances, wherein at least one flow resistance contains a differential pressure sensor and the other flow resistance contains either a differential pressure sensor or a mass flow sensor and which are connected in series, wherein the at least two flow resistances have different characteristic curves, and
    b) determining the fluid concentration by determining the respective pressure drop over the flow resistances by means of a calibration curve.

7. The method according to claim 6, wherein one of the flow resistances has a linear characteristic curve and another flow resistance has a square characteristic curve.

8. The method according to claim 6 or 7 wherein one flow resistance is formed by a sintered metal filter and another flow resistance is formed by an orifice.

9. The method according to claim 6, wherein one of the flow resistances includes a thermal mass flow sensor.

10. The method according to claim 6, wherein the fluid mixture is gaseous.

11. The method according to claim 10, wherein the fluid mixture contains CO2 and air.

* * * * *